United States Patent
Yamaguchi

(10) Patent No.: US 10,039,740 B2
(45) Date of Patent: Aug. 7, 2018

(54) THERAPEUTIC COMBINATIONS OF SESQUITERPENES AND FLAVONOIDS

(71) Applicant: Primus Pharmaceuticals, Inc., Scottsdale, AZ (US)

(72) Inventor: Masayoshi Yamaguchi, Shizuoka (JP)

(73) Assignee: Primus Pharmaceuticals, Inc., Scottsdale, AZ (US)

( * ) Notice: Subject to any disclaimer, the term of this patent is extended or adjusted under 35 U.S.C. 154(b) by 0 days.

(21) Appl. No.: 15/293,354

(22) Filed: Oct. 14, 2016

(65) Prior Publication Data

US 2017/0112802 A1  Apr. 27, 2017

Related U.S. Application Data

(60) Provisional application No. 62/245,350, filed on Oct. 23, 2015.

(51) Int. Cl.
| | | |
|---|---|---|
| *A01N 43/16* | (2006.01) | |
| *A61K 31/35* | (2006.01) | |
| *A61K 31/353* | (2006.01) | |
| *A61K 31/015* | (2006.01) | |
| *A61K 9/00* | (2006.01) | |
| *A61K 31/352* | (2006.01) | |

(52) U.S. Cl.
CPC .......... *A61K 31/353* (2013.01); *A61K 9/0053* (2013.01); *A61K 31/015* (2013.01); *A61K 31/352* (2013.01)

(58) Field of Classification Search
None
See application file for complete search history.

(56) References Cited

U.S. PATENT DOCUMENTS

2008/0280996 A1* 11/2008 Pianowski ........... A61K 31/015
514/763

OTHER PUBLICATIONS

Levy et al. (Nutrition Research, 2009, 29, 298-304).*
Flavocoxid (Mayo Clinic, 2017, http://www.mayoclinic.org/drugs-supplements/flavocoxid-oral-route/description/drg-20067393).*
Veturini et al. (Food Technol. Biotechnol. 2014, 52, 403-410).*
Izumi, et al., "Overexpression of regucalcin suppresses cell death in cloned rat hepatoma H4-II-E cells induced by tumor necrosis factor-alpha or thapsigargin.", J Cell Biochem., 15;92(2):296-306, May 2004.
Yamaguchi, et al., Overexpression of Regucalcin Suppresses Cell Proliferation in Cloned Rat Hepatoma H4-II-E Cells: Involvement of Intracellular Signaling Factors and Cell Cycle-Related Genes, Journal of Cellular Biochemistry, 95:1169-1177, 2005.
Yamaguchi, et al., "The bone anabolic carotenoid p-hydroxycinnamic acid promotes osteoblast mineralization and suppresses osteoclast differentiation by antagonizing NF-κB activation", International Journal of Molecular Medicine, 30: 708-712, 2012.
Yamaguchi, et al., "Suppression of NF-κB Activation by Gentian Violet Promotes Osteoblastogenesis and Suppresses Osteoclastogenesis", Curr Mol Med., 14(6): 783-792, 2014.

* cited by examiner

*Primary Examiner* — Daniel M Podgorski
(74) *Attorney, Agent, or Firm* — Clark G. Sullivan

(57) ABSTRACT

Provided is a pharmaceutical formulation and a method associated therewith for treating inflammation. The pharmaceutical formulation includes therapeutically effective amounts of sesquiterpenes such as β-caryophyllene and two flavonoids. The two flavonoids include baicalin and catechin.

9 Claims, 13 Drawing Sheets

US 10,039,740 B2

THERAPEUTIC COMBINATIONS OF SESQUITERPENES AND FLAVONOIDS

FIELD OF THE INVENTION

The present invention relates to inflammation, and novel combinations of active ingredients useful and synergistic for treating or preventing inflammation.

BACKGROUND OF THE INVENTION

Flavonoids are a diverse class of compounds found in a large variety of plants and herbs that have shown some benefit on human health. For example, U.S. Patent Publication 2013/0210753 describes methods for treating muscular dystrophies using flavonoids.

Baicalin and catechin are two types of flavonoids. Baicalin and catechin are the principal active ingredients in Limbrel®, a medical food marketed by Primus Pharmaceuticals, Inc., Scottsdale Ariz., for the management of metabolic processes that underlie osteoarthritis. Limbrel® is supplied as an oral capsule, and contains from 250 to 500 mg of baicalin and catechin combined, for administration once or twice daily.

β-Caryophyllene is a natural sesquiterpene found in the essential oils of a variety of plants, including clove, hemp *Cannabis sativa*, rosemary *Rosmarinus oficinalis, Cinnamonum* sp. (cinnamon) and hops. β-Caryophyllene has been approved as a food additive by the United States Food and Drug Administration (FDA), and is widely used in foods as a flavor and aroma enhancer.

The aim of this work was to investigate the effects of a sesquiterpene such as β-Caryophyllene, baicalin, (+)-catechin and other plant derived substances on RAW267.4 cells (macrophage) in vitro, and to develop a method and a pharmaceutical formulation that can effectively treat inflammation.

SUMMARY OF THE INVENTION

It has surprisingly been discovered that the combination of sesquiterpenes such as β-caryophyllene, baicalin, and catechin is synergistically effective at reducing proliferation of inflammatory cells, and can be used in the treatment of numerous diseases in which inflammation is involved, including osteoarthritis and rheumatoid arthritis. Based on this discovery, numerous products and methods of treatment are now possible.

One aspect of the present invention relates to a pharmaceutical formulation or unit dosage form for the treatment or management of inflammatory processes. The pharmaceutical formulation or unit dosage form includes therapeutically effective amounts of a sesquiterpene such as β-caryophyllene and two flavonoids, preferably baicalin and catechin.

Another aspect of the present invention relates to a method of treating inflammation or managing inflammatory processes in a human being in need thereof. The method includes administering to the human being a pharmaceutical formulation or unit dosage form comprising therapeutically effective amounts of a sesquiterpene such as β-caryophyllene and two flavonoids, preferably baicalin and catechin.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The following detailed description of the invention is better understood when read in conjunction with the appended drawings. The figures show exemplary embodiments, but the subject matter is not limited to the specific elements and instrumentalities disclosed.

DETAILED DESCRIPTION OF THE INVENTION

1. Definitions and Use of Terms

Figure 1:
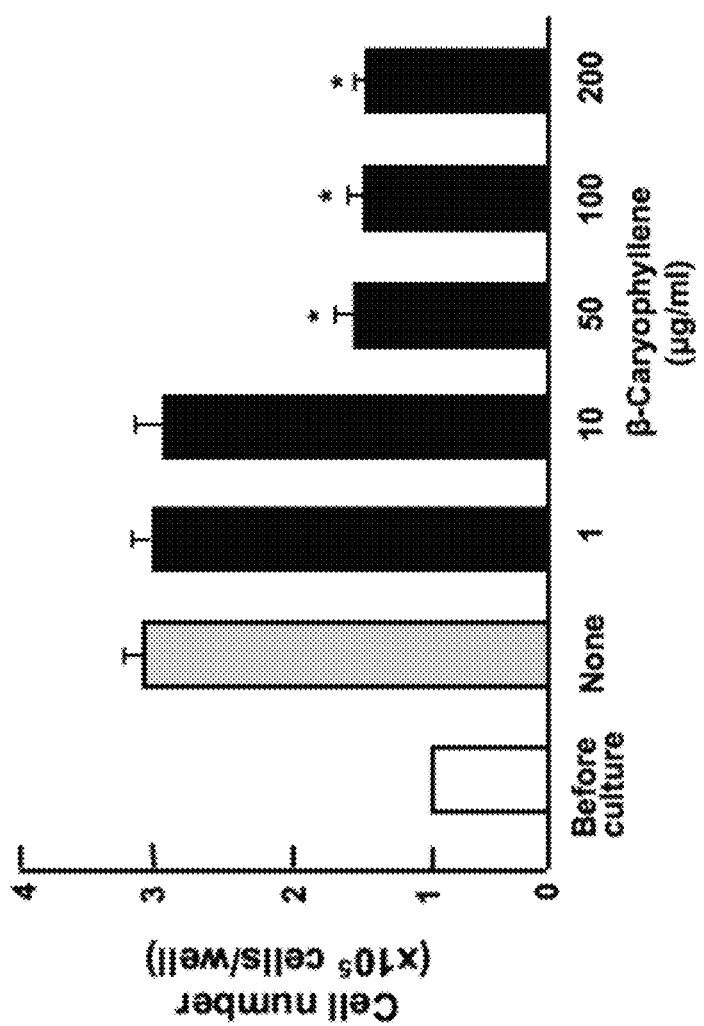
FIG. 1 is a graph showing the effects of β-caryophyllene on the proliferation of RAW267.4 cells in vitro.

As used in this specification and in the claims, which follow, the singular forms "a," "an" and "the" include plural referents unless the context clearly dictates otherwise.

"Therapeutically effective amount" means that amount which, when administered to an animal for treating or preventing a disease, or for supporting or affecting a metabolic process, is sufficient to effect such treatment or prevention of the disease, or supporting or affecting the metabolic process.

When ranges are given by specifying the lower end of a range separately from the upper end of the range, or specifying particular numerical values, it will be understood that a range can be defined by selectively combining any of the lower end variables, upper end variables, and particular numerical values that is mathematically possible.

When used herein the term "about" will compensate for variability allowed for in the pharmaceutical industry and inherent in pharmaceutical products, such as differences in product strength due to manufacturing variation and time-induced product degradation. The term allows for any variation, which in the practice of pharmaceuticals would allow the product being evaluated to be considered bioequivalent in humans to the recited strength of a claimed product.

In the context of the present invention insofar as it relates to any of the disease conditions recited herein, the term "treatment" means to reduce the occurrence of a symptom or condition, or to relieve or alleviate at least one symptom associated with such condition, or to slow or reverse the progression of such condition, or to manage or affect the metabolic processes underlying such condition. Within the meaning of the present invention, the terms also denotes to arrest, delay the onset (i.e., the period prior to clinical manifestation of a disease) and/or reduce the risk of developing or worsening a disease.

The phrase "pharmaceutically acceptable", as used in connection with compositions of the invention, refers to molecular entities and other ingredients of such compositions that are physiologically tolerable and do not typically produce untoward reactions when administered to a subject (e.g., a mammal such as a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

Sesquiterpenes are a class of terpenes that consist of three isoprene units and have the empirical formula $C_{15}H_{24}$. Like monoterpenes, sesquiterpenes may be acyclic or contain rings, including many unique combinations. Biochemical modifications such as oxidation or rearrangement produce the related sesquiterpenoids, which are further included within the definition of sesquiterpenes herein. Suitable sesquiterpenes can be monocyclic, bicyclic or tricyclic. Sesquiterpenes with macrocyclic rings, such as humulene. Suitable ring structures are defined by the cadinenes, which contain two fused six membered rings, as well as aromatic bicyclic sesquiterpenoids such as vetivazulene and guaiazulene. A particularly preferred ring structure is the nine-membered ring fused to a cyclobutane ring structure that characterizes β-caryophyllene, a component of many essential oils such as clove oil. Compounds useful in the present invention can be created from any of the base ring structure of the foregoing molecules, with varying degrees of ethylenic unsaturation, and varying levels of methyl substitution.

The structure for β-caryophyllene is presented below. It will be understood that positional isomers and stereoisomers of β-caryophyllene can be employed, as well as structural isomers in which two or more methyl moieties are substituted by ethyl, and congeners differing in the degree of ethylenic saturation.

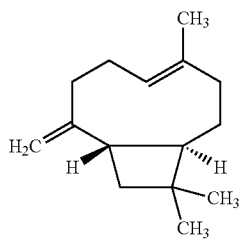

As used herein, the term "subject" refers to any mammal. In a preferred embodiment, the subject is human.

Throughout the description and claims of this specification, the word "comprise" and variations of the word, such as "comprising" and "comprises," means "including but not limited to," and is not intended to exclude, for example, other additives, components, integers or steps.

2. Pharmaceutical Formulations and Methods of Treatment

The present invention relates to a pharmaceutical formulation or unit dosage form for treating inflammation, reducing nociceptive symptoms associated with inflammatory processes, or otherwise influencing the metabolic processes that underlie inflammation. The pharmaceutical formulation or unit dosage form may include β-caryophyllene and other compounds that achieve an antioxidant effect, an anti-inflammatory effect, or a combination of both effects.

The pharmaceutical formulation includes a at least one sesquiterpene such as β-caryophyllene and one or more flavonoids, preferably baicalin and catechin. β-caryophyllene, baicalin and (+)-catechin may act as an anti-inflammatory agent. Such composition may have a potent synergistic-suppressive effect on cell proliferation in vitro. By way of example, such composition may have a potent synergistic-suppressive effect on RAW267.4 cells (macrophage) in vitro. Activation of RAW267.4 cells is an in vitro model of inflammatory processes.

Each active ingredient in the composition may be present in a different dose. A therapeutically effective amount of the at least one sesquiterpene such as β-caryophyllene typically ranges from about 10 to about 1500 mg/day. For example, β-caryophyllene may be administered at 100-1000 mg/day for 2 to 4 days for loading, and may be then reduced by half for chronic administration. Preferred loading ranges are about 200-800 and 300-500 mg/day or about 400 mg/day. Preferred chronic ranges are from about 50 to about 500 and from about 100 to about 300 mg/day, preferably 200 mg/day.

A single dosage form will commonly contain from about 100 to about 800 mg, from about 100 to about 300 mg, from about 300 to about 500 mg, or from about 500 to about 800 mg of at least one sesquiterpene, preferably β-caryophyllene.

The flavonoids such as baicalin and catechin are typically evaluated as a combination. A therapeutically effective amount of this combination typically ranges from about 10 to about 1500 mg/day. In one example, this combination may have, but is not limited to, any one of the following ranges: from about 10 to about 1000 mg/day, from about 100 to about 500 mg/day, from about 500 to about 900 mg/day, from about 200 to about 400 mg/day, from about 600 to about 800 mg/day, from about 300 to about 700 mg/day, and from about 200 to about 1000 mg/day.

The combined amount of baicalin and catechin in a unitary dosage form will typically range from 100 to 800 mg, but preferably ranged from 200 to 300 mg or from 400 to 600 mg, must preferably 250 mg or 500 mg. The ratio of baicalin to catechin may be, but not limited to, any one of the following ratios: from about 10:1 to about 1:10, from about 10:1 to about 2:1, from about 1:2 to about 1:10, from about 1:5 to about 5:1, and from about 90:10 to about 10:90. In one example, the ratio of baicalin to catechin may be from about 8:1 to about 1:2. In all the embodiments of the present invention, the catechin is preferably present as (+)-catechin.

The foregoing doses can be administered in any dosing regimen, including once or twice daily. When administered twice daily, one half of the daily dose will preferably be administered with each dose.

In one embodiment, the composition may suppress production of TNF-α and IL-1β in RAW267.4 cells. In another embodiment, β-caryophyllene, baicalin and (+)-catechin may suppress NF-κB activation induced by inflammatory cytokines.

According to one aspect of the present technology, a method of treating inflammation (or affecting the metabolic processes underlying inflammation) may include providing a pharmaceutical composition comprising a therapeutically effective amount of β-caryophyllene and flavonoids, and administering the composition to a subject, preferably a human being. The flavonoids preferably include baicalin and catechin.

A pharmaceutical composition is formulated to be compatible with its intended route of administration. Examples of suitable routes of administration include parenteral, oral, transmucosal, and rectal administration. The compounds for use in the method of the invention can be formulated for administration by any suitable route, such as for oral or parenteral, for example, transmucosal (e.g., sublingual, lingual, (trans)buccal), nasal, (trans)dermal, and (trans)rectal) administration.

Suitable compositions and dosage forms include tablets, capsules, caplets, pills, gel caps, troches, dispersions, suspensions, solutions, syrups, granules, beads, gels, powders, pellets, magmas, lozenges, discs, suppositories, liquid sprays, or dry powders.

It is preferred that the compounds are orally administered. Suitable oral dosage forms include, for example, tablets, capsules or caplets prepared by conventional means with pharmaceutically acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrates (e.g., sodium starch glycolate); or wetting agents (e.g., sodium lauryl sulphate).

If desired, the tablets can be coated, e.g., to provide for ease of swallowing or to provide a delayed release of active, using suitable methods. Liquid preparation for oral administration can be in the form of solutions, syrups or suspensions. Liquid preparations (e.g., solutions, suspensions and syrups) are also suitable for oral administration and can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

3. Experiments Conducted

Various experiments were conducted to determine effects of various active ingredients on RAW 267.4 in vitro. RAW267.4 cells refer to a mouse macrophage that produces various inflammatory cytokines including TNF-α and IL-1β.

3.1 Materials

The following materials were used during the experiments: RAW267.4 (murine macrophage) cells, β-caryophyllene, baicalin, (+)-catechin, curcumin, (+)-aromatic turmerone, Dulbecco's Modification of Eagle's Medium (DMEM) with 4.5 g/L glucose, L-glutamine and sodium pyruvate and antibiotics (penicillin and streptomycin), fetal bovine serum (FBS), and one or more other reagents. Reagents were dissolved in 100% ethanol or dimethyl sulfoxide for use in these experiments.

3.2 Cell Proliferation

RAW267.4 cells may be prepared as $1 \times 10^5$/ml per well. These cells were cultured using a 24-well plate in DMEM containing 10% FBS and 1% P/S for 1, 2, 3 or 7 days in a water-saturated atmosphere containing 5% $CO_2$ and 95% air at 37° C. RAW267.4 cells were cultured DMEM containing 10% FBS and 1% P/S in the presence of β-caryophyllene [1 (5 μM), 10, 50, 100 or 200 μg/ml of medium], baicalin [1 (2.24 μM), 10, 50, 100 or 200 μg/ml of medium], (+)-catechin [1 (3.45 μM), 10, 50, 100 or 200 μg/ml of medium], curcumin [1 (2.72 μM), 10, 50, 100 or 200 μg/ml of medium], or (+)-aromatic turmerone [1 (4.62 μM), 5, 10, 25 or 50 μg/ml of medium] for 3 days. After culture, cells were detached from each culture dish and counted.

3.3 Cell Death

RAW267.4 cells ($1 \times 10^5$/ml per well) were cultured using a 24-well plate in DMEM containing 10% FBS and 1% P/S for 3 days until reaching confluence, and then the cells were cultured another for 2 days in the presence or absence of β-caryophyllene (1 or 10 μg/ml of medium) and/or baicalin or (+)-catechin (1 or 10 μg/ml of medium). After culture, cells were detached from each culture dish.

3.4 Cell Counting

After trypsinization of each culture dish using 0.2% trpysin plus 0.02% EDTA in $Ca^{2+}/Mg^{2+}$-free PBS for 2 min at 37° C., detached cells from the dish were collected after centrifugation. Cells were resuspended in PBS solution and stained with eosin. Cell numbers were counted under a microscope using a Hemocytometer plate. Each dish was counted twice, and an average of two counts was calculated. Cell number was shown as number per well of plate.

3.5 Statistical Analysis

Statistical significance was determined using GraphPad InStat version 3 for Windows XP (GraphPad Software Inc. La Jolla, Calif.). Multiple comparisons were performed by one-way analysis of variance (ANOVA) with Tukey-Kramer multiple comparisons post test for parametric data as indicated. $P<0.05$ was considered statistically significant.

3.6 Experimental Results

The cells were cultured for 3 days in the presence of one or more various compounds to determine their anti-inflammatory effects.

In a first example, RAW267.4 cells were cultured for 3 days in the presence of β-caryophyllene. Various concentrations for β-caryophyllene were used, including 1, 10, 50, 100, and 200 μg/ml of medium. FIG. 1 illustrates cell numbers before culturing, as well as cell numbers after culturing with β-caryophyllene of different concentrations. As shown in FIG. 1, proliferation of RAW267.4 cells was suppressed in the presence of β-caryophyllene of 50, 100, and 200 μg/ml of medium. In FIG. 1, data are presented as mean±SD of 2 replicate wells per data set using different dishes and cell preparation. *$p<0.001$ as compared with control (none) group (grey bar). 1 way ANOVA, Tukey-Kramer post-test.

Figure 2:
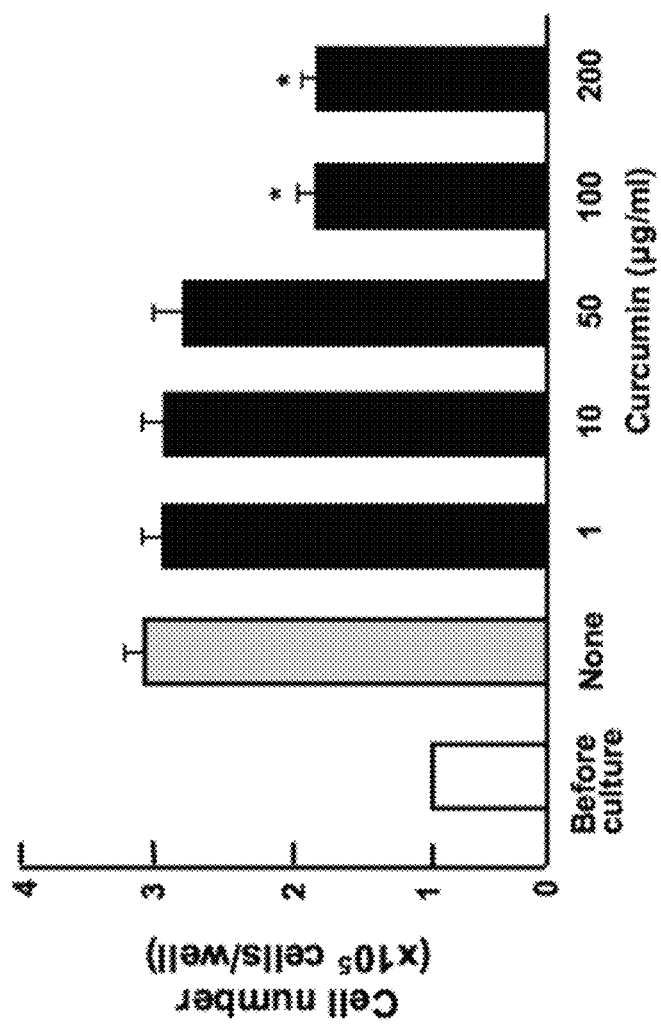
FIG. 2 is a graph showing the effects of curcumin on the proliferation of RAW267.4 cells in vitro.

In a second example, RAW267.4 cells were cultured for 3 days in the presence of curcumin. Various concentrations for curcumin of were used, including 1, 10, 50, 100, and 200 μg/ml. FIG. 2 illustrates cell numbers before culturing, as well as cell numbers after culturing with curcumin of different concentrations. As shown in FIG. 2, proliferation of RAW267.4 cells was suppressed in the presence of curcumin of 100 and 200 μg/ml. In FIG. 2, data are presented as mean±SD of 2 replicate wells per data set using different dishes and cell preparation. *$p<0.001$ as compared with control (none) group (grey bar). 1 way ANOVA, Tukey-Kramer post-test.

Figure 3:
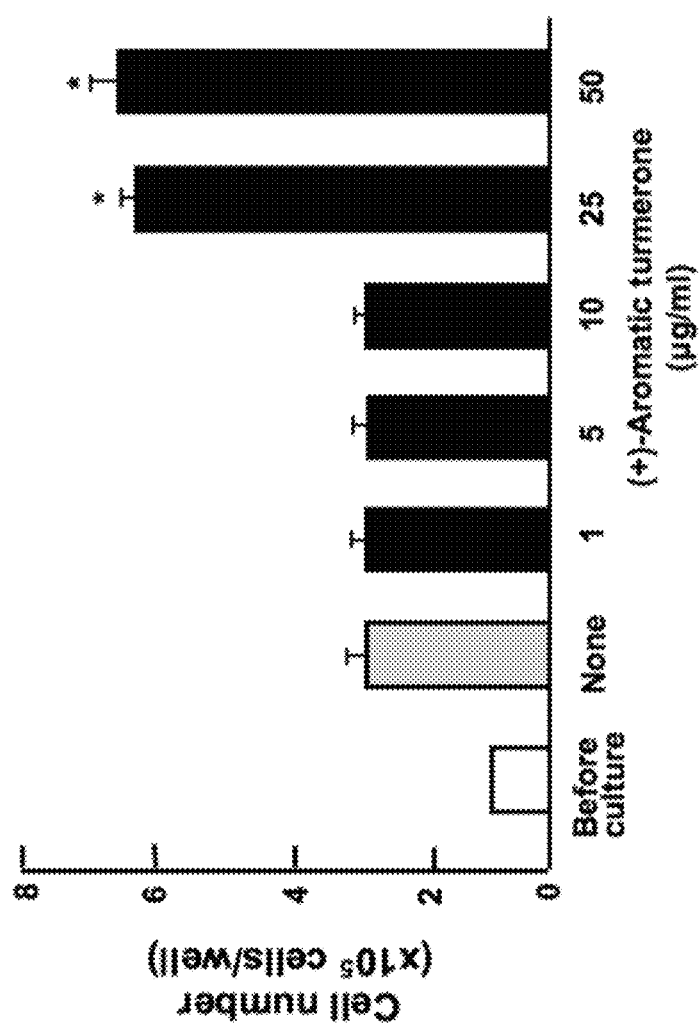
FIG. 3 is a graph showing the effects of (+)-aromatic turmerone on the proliferation of RAW267.4 cells in vitro.

In a third example, RAW267.4 cells were cultured for 3 days in the presence of (+)-aromatic turmerone. Various concentrations for aromatic turmerone were used, including 1, 5, 10, 25 and 50 μg/ml. FIG. 3 illustrates cell numbers before culturing, as well as cell numbers after culturing with aromatic turmerone of different concentrations. As shown in FIG. 3, proliferation of RAW267.4 cells significantly increased in the presence of aromatic turmerone of 25 and 50 μg/ml. In FIG. 3, data are presented as mean±SD of 2 replicate wells per data set using different dishes and cell preparation. *p<0.001 as compared with control (none) group (grey bar). 1 way ANOVA, Tukey-Kramer post-test.

Figure 4:
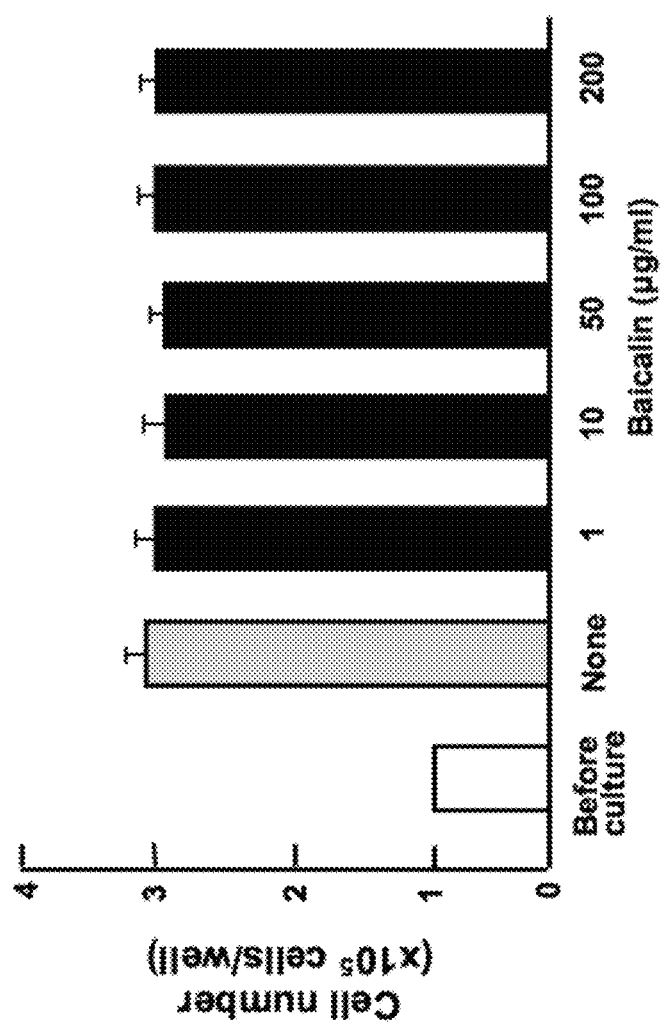
FIG. 4 is a graph showing the effects of baicalin on the proliferation of RAW267.4 cells in vitro.

In a fourth example, RAW267.4 cells were cultured for 3 days in the presence of baicalin. Various concentrations of baicalin were used, including 1, 10, 50, 100, and 200 μg/ml. FIG. 4 illustrates cell numbers before culturing, as well as cell numbers after culturing with baicalin of different concentrations. As shown in FIG. 4, baicalin did not result in a significant effect on RAW267.4 cells. In FIG. 4, data are presented as mean±SD of 2 replicate wells per data set using different dishes and cell preparation. Each value was not a significant difference as compared with the control (none) group (grey bar). 1 way ANOVA, Tukey-Kramer post-test.

Figure 5:
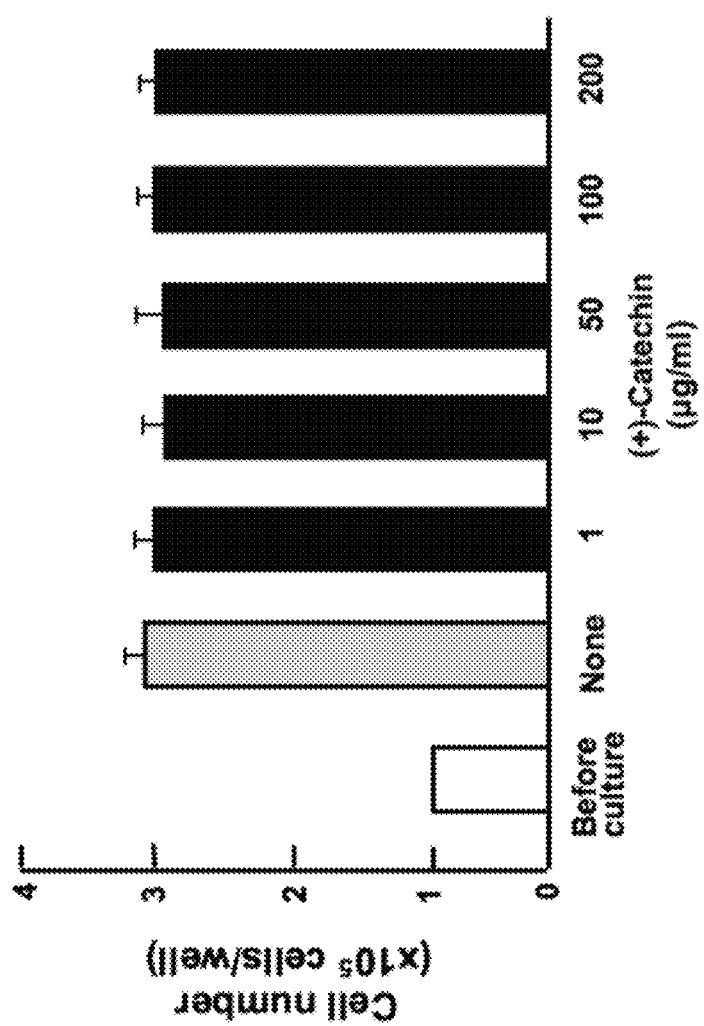
FIG. 5 is a graph showing the effects of (+)-catechin on the proliferation of RAW267.4 cells in vitro.

In a fifth example, RAW267.4 cells were cultured for 3 days in the presence of (+)-catechin. Various concentrations of (+)-catechin of were used, including 1, 10, 50, 100, and 200 μg/ml. FIG. 5 illustrates cell numbers before culturing, as well as cell numbers after culturing with (+)-catechin of different concentrations. As shown in FIG. 5, (+)-catechin did not result in a significant effect on RAW267.4 cells. In FIG. 5, data are presented as mean±SD of 2 replicate wells per data set using different dishes and cell preparation. Each value was not a significant difference as compared with the control (none) group (grey bar). 1 way ANOVA, Tukey-Kramer post-test.

Figure 6:
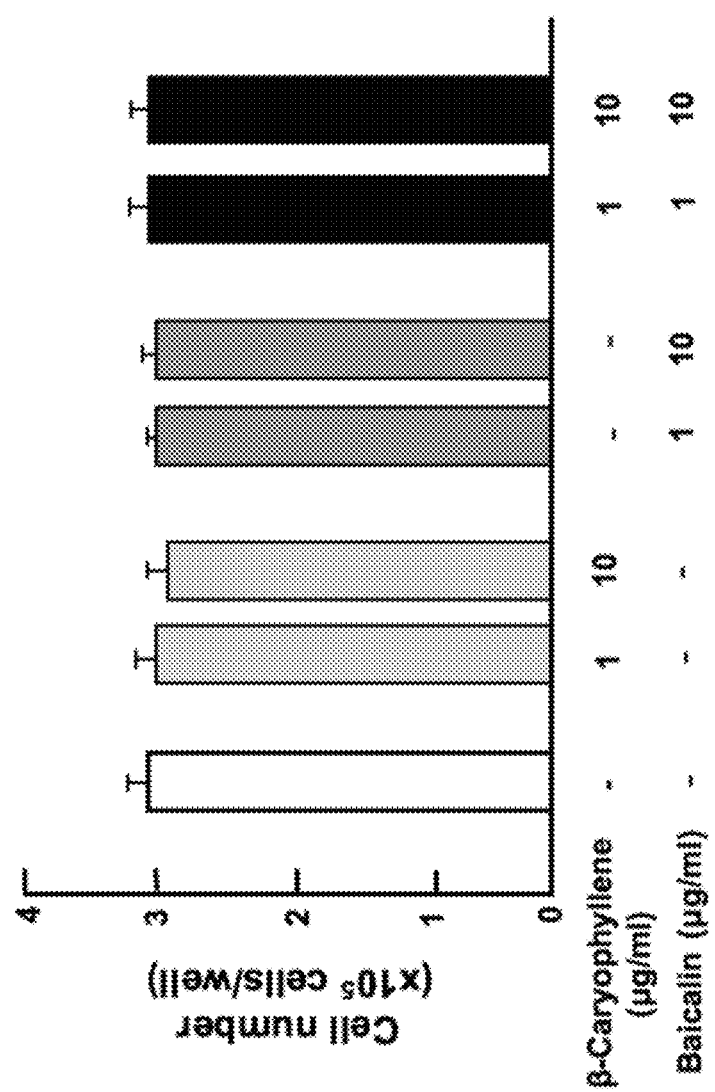
FIG. 6 is a graph showing the effects of the combination of β-caryophyllene and baicalin on the proliferation of RAW267.4 cells in vitro.

In a sixth example, RAW267.4 cells were cultured for 3 days in the presence of a combination of β-caryophyllene and baicalin. Various concentrations for β-caryophyllene and were included, including 1 and 10 μg/ml of each compound. As shown in FIG. 6, the combination of β-caryophyllene and baicalin did not have a significant suppressive on cell proliferation. In FIG. 6, data are presented as mean±SD of 2 replicate wells per data set using different dishes and cell preparation. Treated each value was not a significant difference as compared with control (none) group (grey bar). 1 way ANOVA, Tukey-Kramer post-test.

Figure 7:
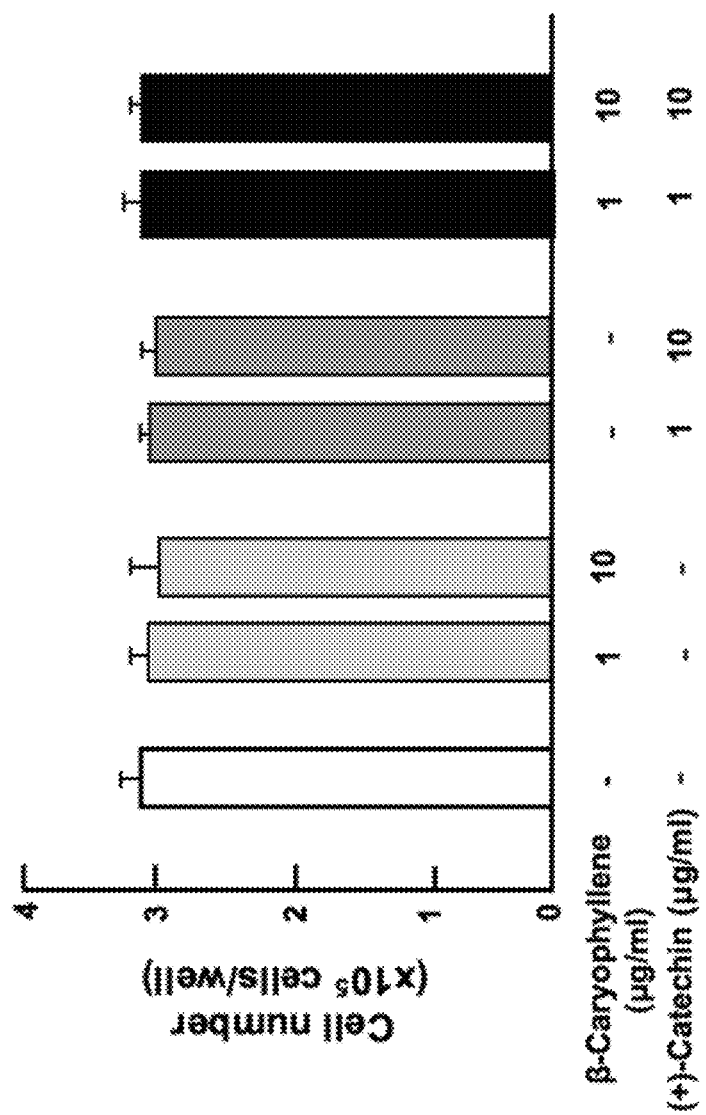
FIG. 7 is a graph showing the effects of the combination of β-caryophyllene and (+)-catechin on the proliferation of RAW267.4 cells in vitro.

In a seventh example, RAW267.4 cells were cultured for 3 days in the presence of a combination of β-caryophyllene and (+)-catechin. Various concentrations of β-caryophyllene and (+)-catechin were used, including 1 and 10 μg/ml of each compound. As shown in FIG. 7, the combination of β-caryophyllene and (+)-catechin did not have a significant suppressive on cell proliferation. In FIG. 7, data are presented as mean±SD of 2 replicate wells per data set using different dishes and cell preparation. Each value was not a significant difference as compared with control (none) group (white bar). 1 way ANOVA, Tukey-Kramer post-test.

Figure 8:
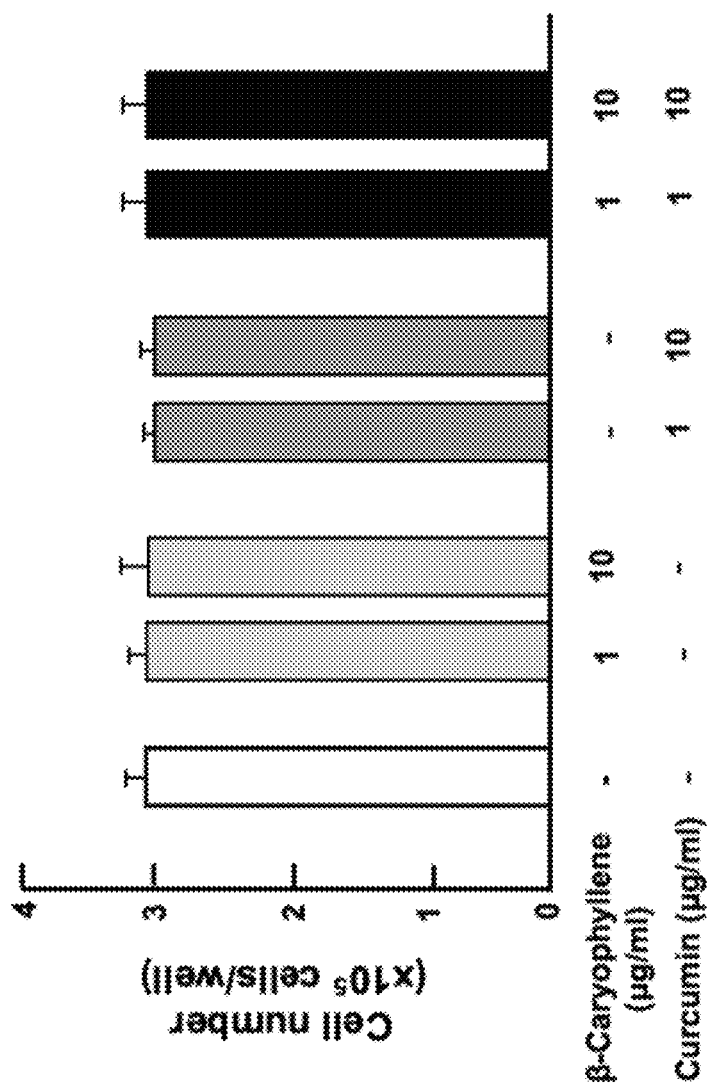
FIG. 8 is a graph showing the effects of the combination of β-caryophyllene and curcumin on the proliferation of RAW267.4 cells in vitro.

In an eighth example, RAW267.4 cells were cultured for 3 days in the presence of a combination of β-caryophyllene and curcumin. Various concentrations of β-caryophyllene and curcumin were used, including 1 and 10 μg/ml for each compound. As shown in FIG. 8, the combination of β-caryophyllene and curcumin did not have a significant suppressive on cell proliferation. In FIG. 8, data are presented as mean±SD of 2 replicate wells per data set using different dishes and cell preparation. Each value was not a significant difference as compared with control (none) group (white bar). 1 way ANOVA, Tukey-Kramer post-test.

Figure 9:
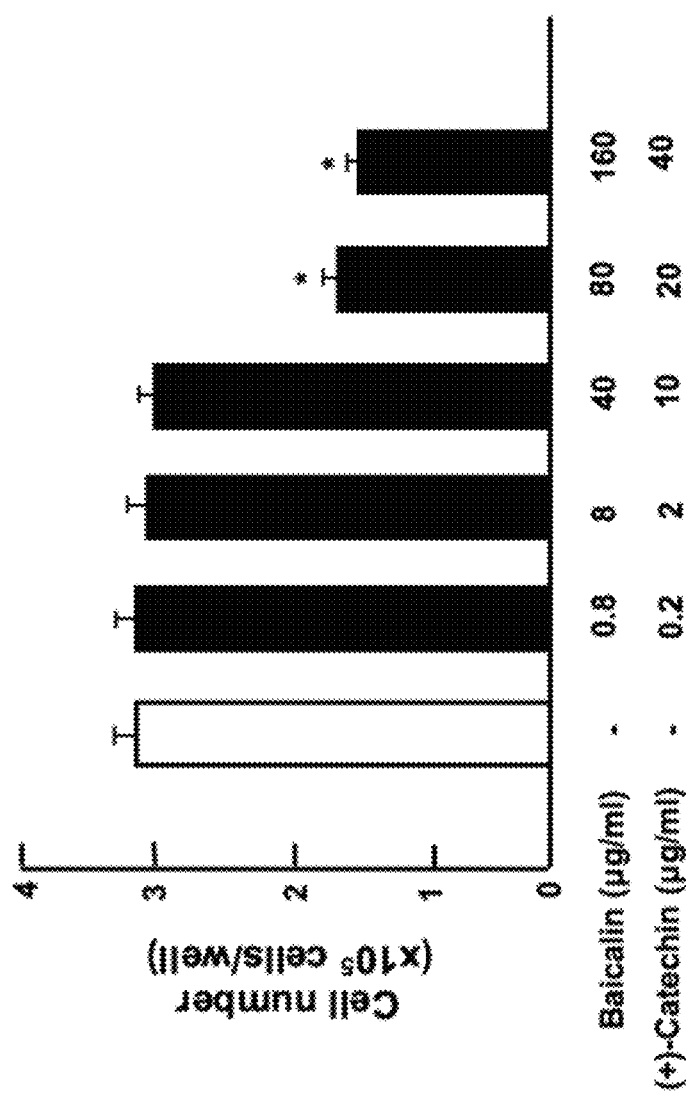
FIG. 9 is a graph showing the effects of the combination of baicalin and (+)-catechin on the proliferation of RAW267.4 cells in vitro.

In a ninth example, RAW267.4 cells were cultured for 3 days in the presence of a combination of baicalin and catechin. Various concentrations for baicalin and (+)-catechin were experimented, including baicalin concentrations of 0.8, 8, 40, 80, and 160 μg/ml, and (+)-Catechin concentrations of 0.2, 2, 10, 20, and 40 μg/ml. As shown in FIG. 9, the combination of baicalin and (+)-catechin at high concentrations caused a significant suppressive effect on cell proliferation, such as baicalin of about 80 or 160 μg/ml, and (+)-catechin of about 20 or 40 μg/ml. On the other hand, the combination of baicalin and (+)-catechin at low concentrations had no significant suppressive effect on cell proliferation, such as baicalin of about 0.8, 8 or 40 μg/ml, and (+)-catechin of about 0.2, 2 or 10 μg/ml. In FIG. 9, data are presented as mean±SD of 2 replicate wells per data set using different dishes and cell preparation. Each value was not a significant difference as compared with control (none) group (white bar). *p<0.001 as compared with control (none) group (white bar). 1 way ANOVA, Tukey-Kramer post-test.

Figure 10:
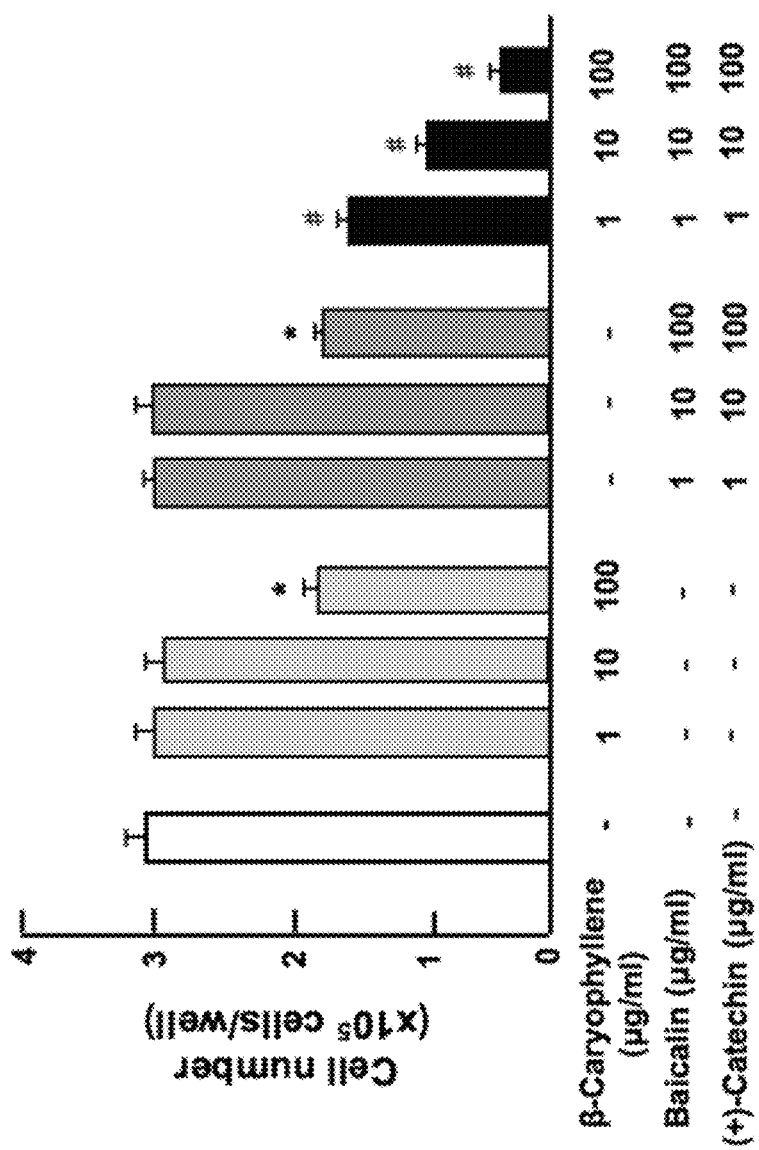
FIG. 10 is a graph showing the effects of the combination of β-caryophyllene, baicalin and (+)-catechin on the proliferation of RAW267.4 cells in vitro.

In a tenth example, RAW267.4 cells were cultured for 3 days in the presence of a combination of β-caryophyllene, baicalin and catechin. Various concentrations for β-caryophyllene, baicalin and (+)-catechin were tested, including 1, 10 and 100 μg/ml for each compound. As shown in FIG. 10, β-caryophyllene alone at low concentrations such as 1 or 10 μg/ml did not result any significant suppressive effect on cell proliferation. Similarly, the combination of baicalin and (+)-catechin each at low concentrations such as 1 or 10 μg/ml also failed to cause any significant suppressive effect on cell proliferation. However, the combination of β-caryophyllene, baicalin and (+)-catechin each at low concentrations such as 1 or 10 μg/ml revealed a potent synergistic-suppressive effect on the proliferation. Such an effect was also seen in the case of the higher concentration, e.g., about 100 μg/ml, of β-caryophyllene, baicalin and (+)-catechin. Therefore, the proliferation of RAW267.4 cells was synergistically suppressed by the combination of β-caryophyllene, baicalin and (+)-catechin. In FIG. 10, data are presented as mean±SD of 2 replicate wells per data set using different dishes and cell preparation. Each value was not a significant difference as compared with control (none) group (white bar). *p<0.001 as compared with control (none) group (white bar). #p<0.001 as compared with the group of β-caryophyllene (1, 10, and 100 μg/ml of medium) or baicalin, (+)-catechin (1, 10 or 100 μg/ml of medium) alone. 1 way ANOVA, Tukey-Kramer post-test.

Figure 11:
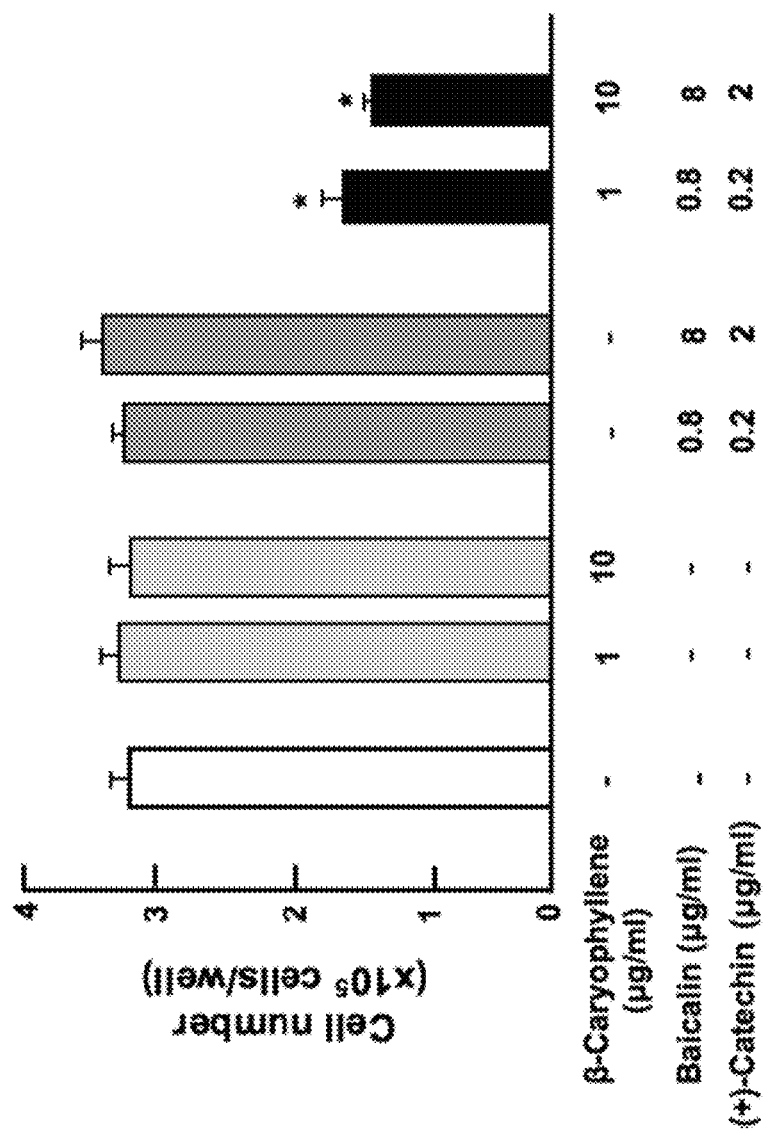
FIG. 11 is a graph showing the effects of the combination of β-caryophyllene, baicalin and (+)-catechin on the proliferation of RAW267.4 cells in vitro.

In an eleventh example, RAW267.4 cells were cultured for 3 days in the presence of a combination of β-caryophyllene, baicalin and catechin, where β-caryophyllene had concentrations of 1 and 10 μg/ml, baicalin had concentrations of 0.8 and 8 μg/ml, and (+)-catechin had concentrations of 0.2 and 2 μg/ml. As shown in FIG. 11, the combination of β-caryophyllene (1 or 10 μg/ml), baicalin (0.8 or 8 μg/ml) and (+)-catechin (0.2 or 2 μg/ml) revealed a potent synergistic-suppressive effect on cell proliferation. In FIG. 11, data are presented as mean±SD of 2 replicate wells per data set using different dishes and cell preparation. *p<0.001 as compared with control (none) group (white bar), β-caryophyllene, baicalin or (+)-catechin alone. 1 way ANOVA, Tukey-Kramer post-test.

Figure 12:
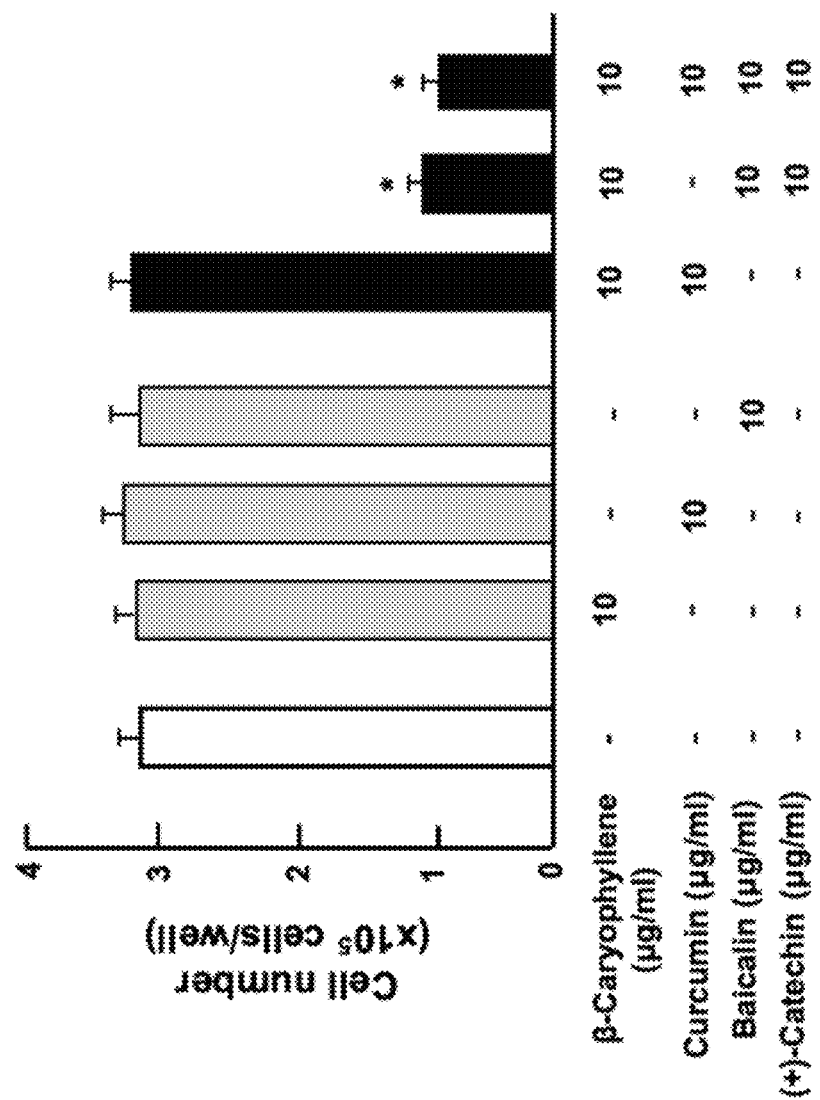
FIG. 12 is a graph showing the effects of the combination of β-caryophyllene, baicalin, (+)-catechin and curcumin on the proliferation of RAW267.4 cells in vitro.

In a twelfth example, RAW267.4 cells were cultured for 3 days in the presence of a combination of β-caryophyllene, baicalin, catechin, and curcumin. Each compound had a concentration of about 10 μg/ml. According to FIG. 12, the addition of curcumin did not change the potent-synergistic suppressive effect. The synergistic effects with the combination of β-caryophyllene, baicalin and (+)-catechin on cell proliferation were not enhanced in the presence of curcumin. Accordingly, the combination of β-caryophyllene, baicalin and (+)-catechin has a potent-synergistic suppressive effect on RAW267.4 cells (macrophage) in vitro. In FIG. 12, data are presented as mean±SD of 2 replicate wells per data set using different dishes and cell preparation. *p<0.001 as compared with control (none) group (white bar), or β-caryophyllene, baicalin, (+)-catechin or curcumin alone. 1 way ANOVA, Tukey-Kramer post-test.

In one example, to determine whether the combination with β-caryophyllene, baicalin and (+)-catechin induces apoptotic cell death in vitro, RAW267.4 cells were cultured using a 24-well plate in DMEM containing 10% FBS and 1% P/S for 3 days until they became confluent. The cells were then additionally cultured for 2 days in the presence of at least one of β-caryophyllene, baicalin, catechin, and curcumin. As shown in FIG. 12, the combination of β-caryophyllene, baicalin and (+)-catechin, or the combination of β-caryophyllene, baicalin, (+)-catechin and curcumin caused a significant decrease in cell number, indicating that this treatment induces cell death.

Figure 13:
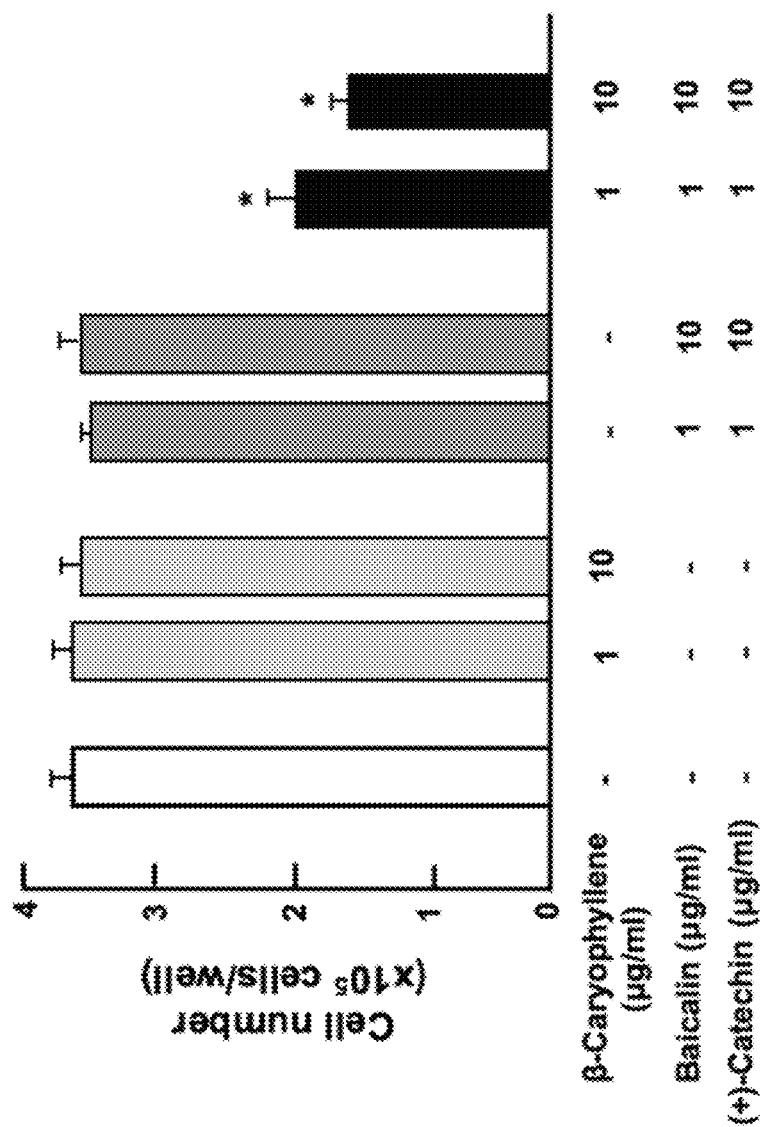
FIG. 13 is a graph showing the effects of the combination of β-caryophyllene, baicalin and (+)-catechin on the death of RAW267.4 cells in vitro.

In another example, RAW267.4 cells were cultured for 3 days without various chemicals, and then cells with subconfluency were additionally cultured for 2 days in the presence of at least one of β-caryophyllene, baicalin and catechin. β-Caryophyllene, baicalin and (+)-catechin each had various concentrations of 1 and 10 μg/ml of medium. As shown in FIG. 13, β-caryophyllene alone did not induce a significant decrease in the number of RAW267.4 cells, whether β-caryophyllene was at about 1 or 10 μg/ml of medium. Also as illustrated in FIG. 13, the combination of baicalin and (+)-catechin in culture medium, without other compounds, failed to induce a significant decrease in the number of RAW267.4 cells, whether baicalin and (+)-catechin were at about 1 or 10 μg/ml of medium. In FIG. 13, data are presented as mean±SD of 2 replicate wells per data set using different dishes and cell preparation. *p<0.001 as compared with control (none) group (white bar) or β-caryophyllene, baicalin, (+)-catechin or curcumin alone. 1 way ANOVA, Tukey-Kramer post-test.

Based on the above experiments, it may be concluded that β-caryophyllene, baicalin and (+)-catechin each alone do not have significant effects on the death of RAW267.4 cells in vitro. However, as shown in the above test results, the combination of β-caryophyllene, baicalin and (+)-catechin caused the death of RAW267.4 cells in vitro. Suppressive effects of β-caryophyllene, baicalin and (+)-catechin on the proliferation of RAW267.4 cells may partly be dependent on a stimulatory effect on cell death. Accordingly, the experiments demonstrate that the combination with β-caryophyllene, baicalin and (+)-catechin have potential synergistic-suppressive effects on macrophages that is related to inflammation with pain.

4. References

The entire disclosures of all publications mentioned herein are incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

(1) Ghelardini C, Galeotti N, Di Cesare Mannelli L, Mazzanti G, Bartolini A (2001) Local anaesthetic activity of beta-caryophyllene. Farmaco 56: 387-389.

(2) Gertsch J, Leonti M, Raduner S, et al. (2008). Beta-caryophyllene is a dietary cannabinoid. Proc Nat Acad Sci USA 105: 9099-9104.

(3) Ormeño E, Baldy V, Ballini C, Fernandez C (2008) Production and diversity of volatile terpenes from plants on calcareous and siliceous soils: effect of soil nutrients. J Chem Ecol 34: 1219-1229.

(4) Iqbal, Mohammed (1993). "International trade in non-wood forest products: An overview". F O: Misc/93/11—Working Paper. Food and Agriculture Organization of the United Nations. Retrieved Nov. 12, 2012

(5) Katsuyama S, Mizoguchi H, Kuwahata H, et al. (2013) Involvement of peripheral cannabinoid and opioid receptors in β-caryophyllene-induced antinociception. Eur J Pain 17: 664-675.

(6) Paula-Freile L I, Andersen M L, Gama V S, Molska G R, Carlini E L (2015) The oral administration of trans-caryophyllene attenuates acute and chronic pain in mice. Phytomedicine 21:356-362.

(7) Chavan M J, Wakte P S, Shinde D B (2010) Analgestic and anti-inflammatory activity of caryophyllene oxide from Annona squamosal L. bark. Phytomedicine 17:149-151.

(8) Martinez R M, Zarpelon A C, Cardoso R D, Vicentini F T, Georgetti S R, Baracat M M, Andrel C C, Moreira I C, Verri W A Jr, Casagrande R (2013) Tephrosia sinapou ethyl acetate extract inhibits inflammatory pain in mice: opioid receptor dependent inhibition of TNFα and IL-1β production. Pharm Biol 51:1262-1271.

(9) Pomari E, Stefanon B, Colitti M (2014) Effect of plant extracts on H2O2-induced inflammatory gene expression in macrophage. J Inflamm Res 27:103-112.

(10) Yamaguchi M, Vikulina T, Arbiser J L, Weitzmann M N (2014) Suppression of NF-κB activation by gentian violet promotes osteoblastogenesis and suppresses osteoclastogenesis. Curr Mol Med 14:783-792.

(11) Yamaguchi M, Weitzmann M N (2012) The bone anabolic carotenoid p-hydroxycinnamic acid promotes osteoblast mineralization and suppresses osteoclast differentiation by antagonizing NF-κB activation. Int J Mol Med 30:708-712.

(12) Izumi T, Yamaguchi M (2004) Overexpression of regucalcin suppresses cell death in cloned rat hepatoma H4-II-E cells induced by tumor necrosis factor-α or thapsigargin. J Cell Biochem 92: 296-306.

(13) Yamaguchi M, Daimon Y (2005) Overexpression of regucalcin suppresses cell proliferation in cloned rat hepatoma H4-II-E cells: Involvement of intracellular signaling factors and cell cycle-related genes. J Cell Biochem 95: 1169-1177.

(14) Izumi T, Yamaguchi M (2004) Overexpression of regucalcin suppresses cell death in cloned rat hepatoma H4-II-E cells induced by tumor necrosis factor-α or thapsigargin. J Cell Biochem 92: 296-306.

The invention claimed is:

1. A unit dosage form comprising:
 a) from 25 to 800 mg of β-caryophyllene, a positional isomer of β-caryophyllene, a stereoisomer of β-caryophyllene, or a congener of β-caryophyllene differing only in the extent of ethylenic unsaturation in the nine member or five member ring;
 b) from 100 to 800 mg of baicalin and catechin.

2. The unit dosage form of claim 1 in the form of an orally administered tablet or capsule.

3. The unit dosage form of claim 1 comprising baicalin and catechin in a combined amount of from about 200 to about 600 mg, and β-caryophyllene in an amount of from about 25 to about 300 mg.

4. The unit dosage form of claim 1 comprising baicalin and catechin in a combined amount of about 500 mg, and β-caryophyllene in an amount of about 100 mg.

5. The unit dosage form of claim 1 wherein said β-caryophyllene, baicalin and catechin are present in synergistically effective amounts.

6. The unit dosage form of claim 1 wherein said β-caryophyllene, baicalin and catechin have a synergistic-suppressive effect on cell proliferation.

7. The unit dosage form of claim 1, wherein baicalin to catechin has any one of the following ratios: from about 10:1 to about 1:10, from about 10:1 to about 2:1, from about 1:2 to about 1:10, from about 1:5 to about 5:1, from about 90:10 to about 10:90, and from about 8:1 to about 1:2.

8. A method of treating inflammation in a human being in need thereof, comprising administering to the human being the unit dosage form of claim 1 twice daily.

9. The method of claim 8, wherein the unit dosage form is in the form of an orally administered tablet or capsule.

\* \* \* \* \*